United States Patent [19]
Boden et al.

[11] Patent Number: 6,051,548
[45] Date of Patent: Apr. 18, 2000

[54] TRIMETHYLCYCLOHEXENYLCYCLOPROPYL KETONES PERFUME COMPOSITION

[75] Inventors: Richard M. Boden, Ocean; Marie R. Hanna, Hazlet, both of N.J.

[73] Assignee: International Flavors & Fragrances Inc., New York, N.Y.

[21] Appl. No.: 09/186,486

[22] Filed: Nov. 5, 1998

[51] Int. Cl.[7] .................................................. A61K 7/46
[52] U.S. Cl. .................................. 512/22; 512/8; 512/25; 512/26; 512/27; 512/20; 512/21
[58] Field of Search .................................. 512/8, 25, 26, 512/27, 22, 20, 21

*Primary Examiner*—C. H. Kelly
*Assistant Examiner*—Monique T. Cole
*Attorney, Agent, or Firm*—Arthur L. Liberman

[57] ABSTRACT

Described are trimethylcyclohexenylcyclopropyl ketones having the structure:

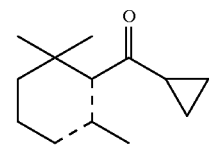

wherein one of the dashed lines is a carbon—carbon double bond and the other of the dashed lines is a carbon—carbon single bond, uses thereof in augmenting, enhancing or imparting aromas in or to perfume compositions, colognes and perfumed articles, and mixtures of same with 3-methyl-1-phenylpentanol-5 and/or butanoylcyclohexane derivatives and/or acetic or propionic acid esters of o-methylphenyl isopropanol.

5 Claims, 5 Drawing Sheets

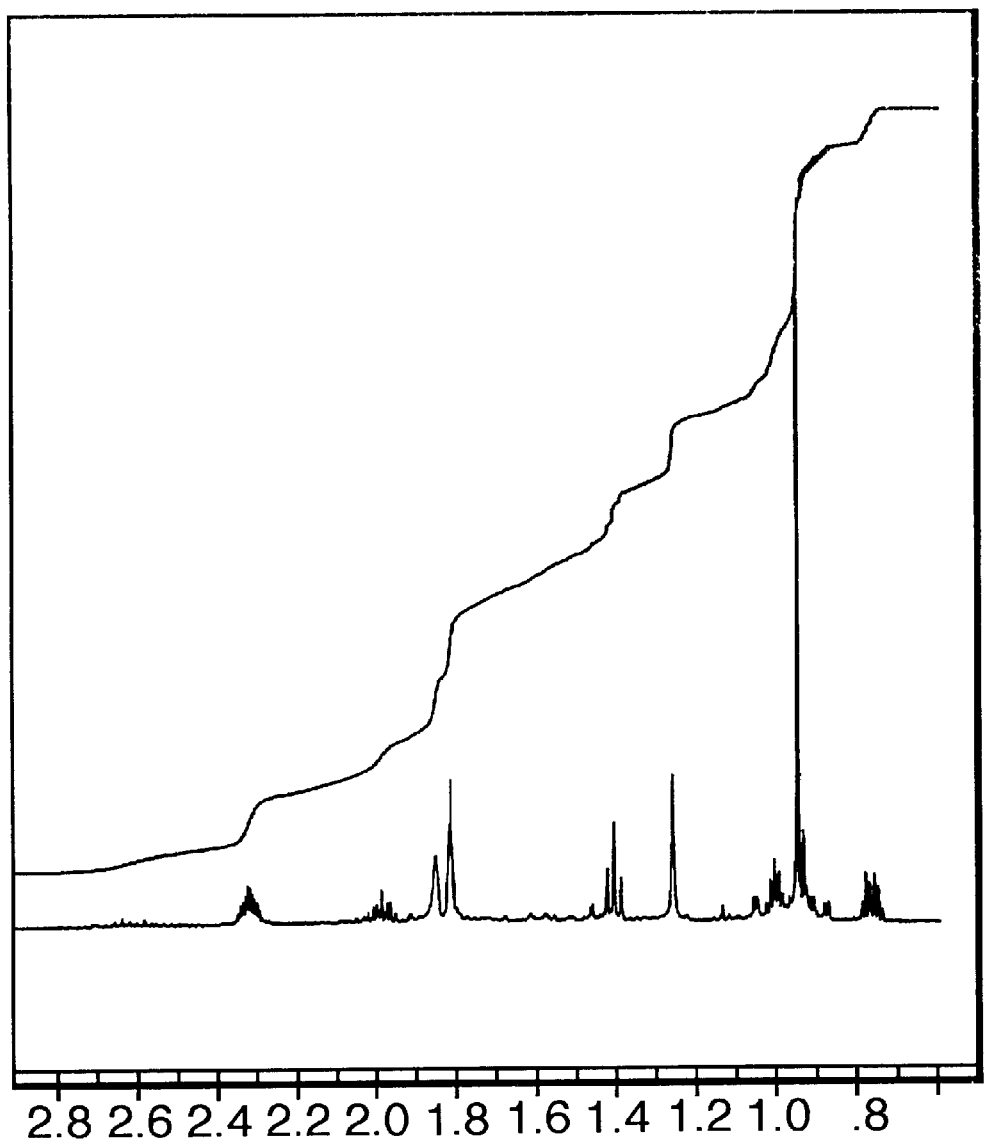
FIG. 2-A

FIG. 2-B
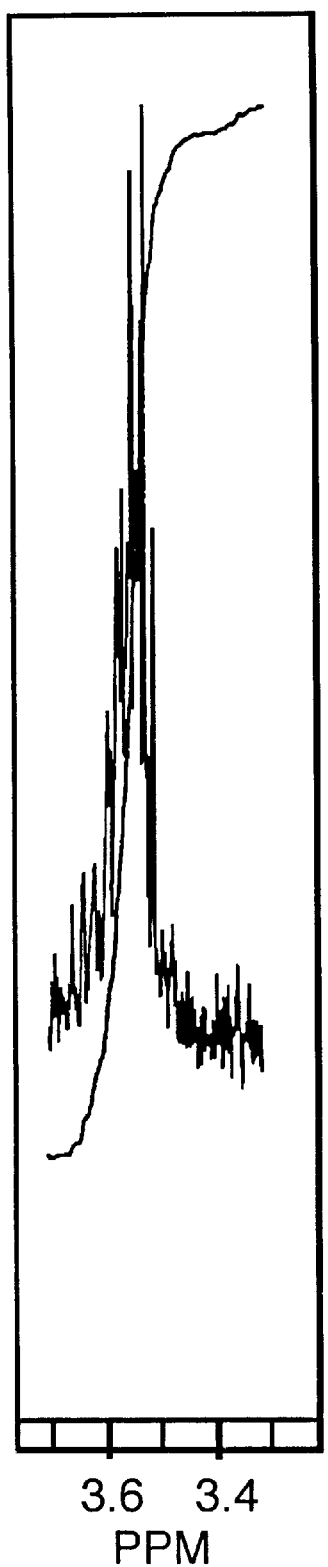

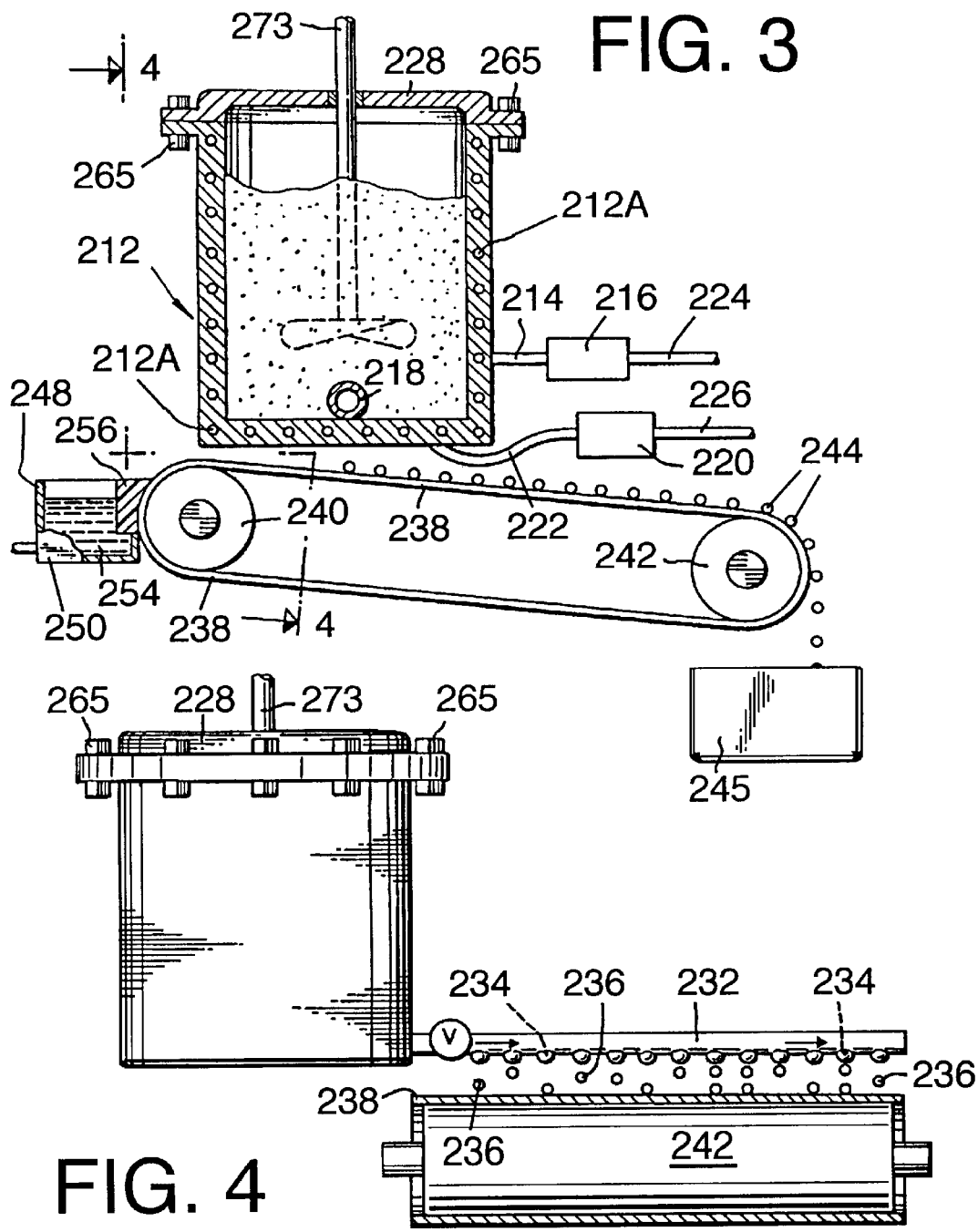

TRIMETHYLCYCLOHEXENYLCYCLOPROPYL KETONES PERFUME COMPOSITION

BACKGROUND OF THE INVENTION

The instant invention relates to trimethylcyclohexenylcyclopropyl ketones defined according to the structure:

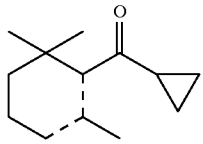

wherein one of the dashed lines is a carbon—carbon double bond and the other of the dashed lines is a carbon—carbon single bond, uses of same in augmenting, enhancing or imparting aromas in or to perfume compositions, colognes and perfumed articles, and mixtures thereof with 3-methyl-1-phenylpentanol-5 and/or butanoylcyclohexane derivatives and/or acetic or propionic acid esters of o-methylphenyl isopropanol.

Inexpensive chemical compounds which are substantive, non-sensitizing and long lasting and which can provide rose, sweet, woody, tobacco and dried fruit aromas with floral undertones are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is, accordingly, a continuous effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions; or they act as sensitizers, for example, to sunlight.

Of particular importance are odorants of the rose type in perfumery, as well as the "woody cologne" type in perfumery.

Cyclopropyl moiety-containing materials are well known in the art of perfumery. Thus, compounds having the generic structure:

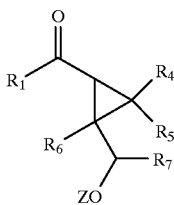

wherein $R_1$, $R_2$ and $R_3$ represent $C_1$–$C_{10}$ alkyl; Z is hydrogen or acyl having the structure:

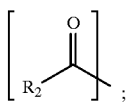

or substituted oxyacyl having the structure:

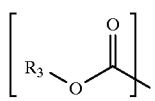

and wherein $R_4$, $R_5$, $R_6$ and $R_7$ represent hydrogen or $C_1$–$C_3$ lower alkyl are disclosed in U.S. Pat. No. 4,536,330 issued on Aug. 20, 1985 for their perfumery uses.

Compounds having the structure:

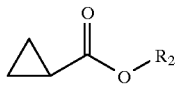

wherein $R_2$ is n-hexyl, cis-3-hexenyl, cyclohexyl methyl or n-heptyl are disclosed for their perfumery uses in of U.S. Pat. No. 5,767,305.

Cyclopropanated campholenic aldehyde derivatives such as that having the structure:

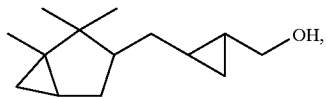

having such aromas as sandalwood, are disclosed in Published European Patent Application No. 801,049 published on Oct. 15, 1997.

Nothing in the prior art, however, discloses the trimethylcyclohexenylcyclopropyl ketones of our invention defined according to the structure:

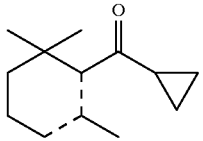

wherein one of the dashed lines is a carbon—carbon double bond and the other of the dashed lines is a carbon—carbon single bond.

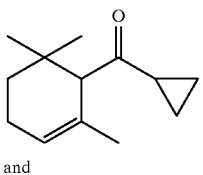

and

-continued

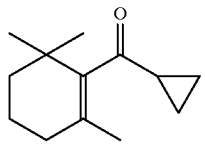

(conditions: SE-30 column programmed from 150–220° C. at 8° C. per minute).

Figure 1:
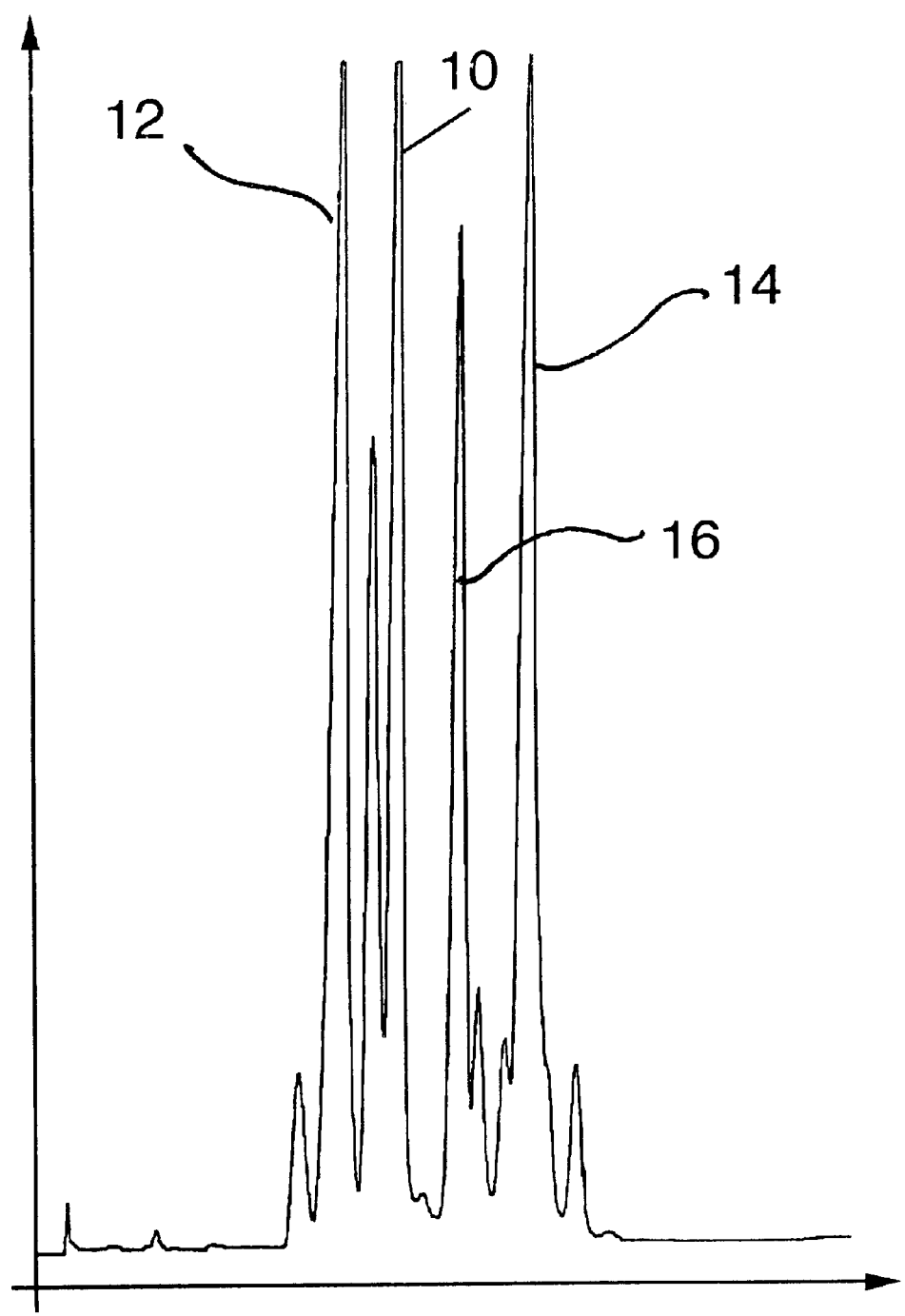
FIG. 1 is the GLC profile for the reaction product of Example I containing a mixture of compounds having the structures.
Figure 2:
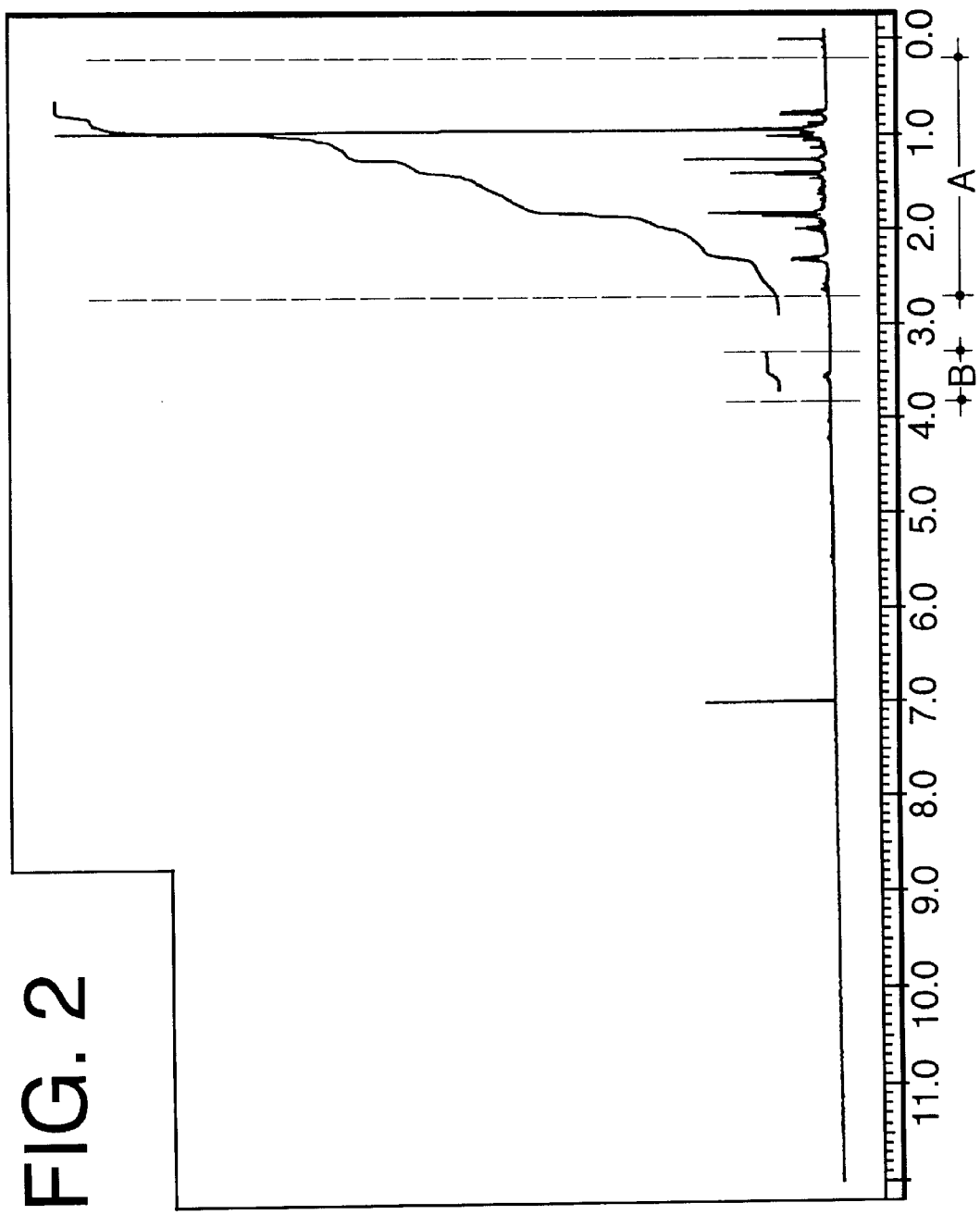

FIG. 2 is the NMR spectrum for the peak indicated by reference numeral 10 of FIG. 1, for the compound having the structure:

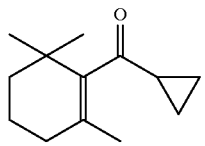

FIG. 2A is an enlargement of section "A" of the NMR spectrum of FIG. 2.

FIG. 2B is an enlargement of section "B" of the NMR spectrum of FIG. 2.

FIG. 3 is a partial side elevation view and partial sectional view of an apparatus for forming polymer pellets containing at least one of the trimethylcyclohexenylcyclopropyl ketones of our invention, taken alone or in admixture with 3-methyl-1-phenylpentanol-5 and/or at least one butanoyl-cyclohexane derivative and/or an acetic or propionic acid ester of o-methylphenyl isopropanol.

FIG. 4 is a section taken along line 4—4 of FIG. 3.

DETAILED DESCRIPTION OF THE DRAWINGS

Referring to FIG. 1, the GLC profile for the reaction product of Example I, the peak indicated by reference numeral 10 is the peak for the compound having the structure:

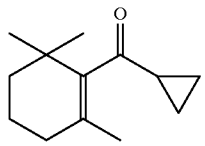

The peak indicated by reference numeral 12 is the peak for the compound having the structure:

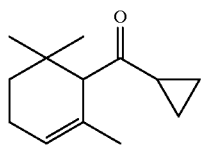

The peak indicated by reference numeral 14 is the peak for the compound having the structure:

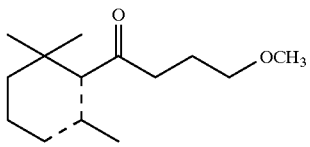

(a byproduct) (a mixture, wherein in the mixture in each of the compounds, one of the dashed lines represents a carbon—carbon double bond and the other of the dashed lines represents a carbon—carbon single bond). The peak indicated by reference numeral 16 is the peak for the mixture of compounds having the structure:

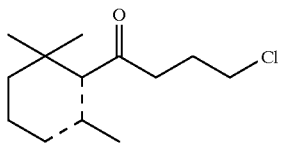

wherein in the mixture in one of the compounds, one of the dashed lines represents a carbon—carbon double bond and the other of the dashed lines represents a carbon—carbon single bond.

Referring to FIGS. 3 and 4, the apparatus used in producing polymeric fragrances containing one or more of the trimethylcyclohexenylcyclopropyl ketones of our invention comprises a device for forming scented polyolefin (for example) pellets, which comprises a vat or container 212 into which a mixture of polyolefin such as polyethylene and an aromatic substance or scented material is placed (in this case, at least one of the trimethylcyclohexenylcyclopropyl ketones of our invention).

The container is closed by an airtight lid 228, and the airtight lid 228 is clamped to the container 212 by bolts 265.

A stirrer 273 traverses the lid or cover 228 in an airtight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 Saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (at least one of the trimethylcyclohexenylcyclopropyl ketones our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the trimethylcyclohexenylcyclopropyl ketones of our invention) are added to the polyolefin.

After the scent imparting material (e.g., a composition containing at least one of the trimethylcyclohexenylcyclopropyl ketones of our invention) is added to the container 212, the mixture is stirred for a few minutes, for example, 5–15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter, the valve V is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., a mixture containing at least one of the trimethylcyclohexenylcyclopropyl ketones of our invention) will continuously drop through orifices 234 downwardly from conduit 232. During this time, the temperature of the polymer (e.g., polyolefin) and aroma imparting material (e.g., a mixture containing at least one of the trimethylcyclohexenylcyclopropyl ketones of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the trimethylcyclohexenylcyclopropyl ketones of our invention) mixture through the orifices 234 at a rate which will insure the formation of droplets 236 which will fall downwardly onto a moving conveyor belt 238 caused to run between conveyor wheels 240 and 242.

When the droplets 236 fall onto the conveyor 238, they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic, but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

THE INVENTION

The present invention provides trimethylcyclohexenylcyclopropyl ketones defined according to the generic structure:

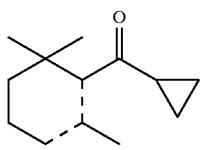

wherein one of the dashed lines represents a carbon—carbon double bond and the other of the dashed lines represents a carbon—carbon single bond.

The trimethylcyclohexenylcyclopropyl ketones of our invention may first be produced as a mixture of compounds having the structures:

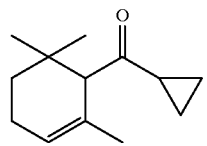

and

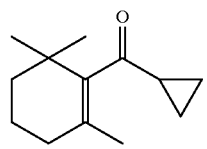

This mixture may then be separated by procedures well known to those having ordinary skill in the art to produce the separate compounds, one having the structure:

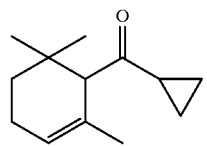

and the other having the structure:

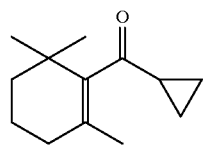

Another aspect of our invention is concerned with mixtures of the trimethylcyclohexenylcyclopropyl ketones of our invention defined according to the structure:

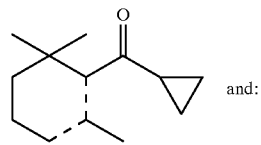 and:

(i) 3-methyl-1-phenylpentanol-5 having the structure:

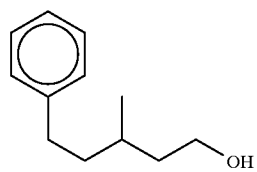

(ii) one or more butanoylcyclohexane derivatives defined according to the generic structure:

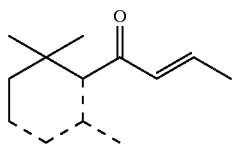

wherein one or two of the dashed lines is a carbon—carbon double bond and the other of the dashed lines is a carbon—carbon single bond with the proviso that when two of the dashed lines are carbon—carbon double bonds, said carbon—carbon double bonds are conjugated;

(iii) an acetic or propionic acid ester of o-methylphenyl isopropanol defined according to the generic structure:

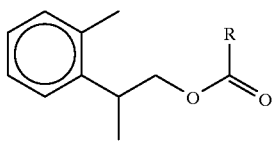

wherein R is methyl or ethyl.

The use of one or both of the trimethylcyclohexenylcyclopropyl ketones of our invention defined according to the structure:

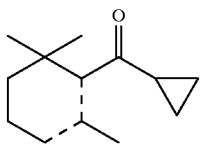

diminishes the need for larger quantities of butanoylcyclohexane derivatives defined according to the structure:

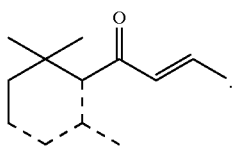

In fact, the cyclopropyl moiety defined according to the structure:

is a replacement from an organoleptic standpoint for the methyl vinyl moiety having the structure:

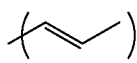

from an organoleptic standpoint. Hence, compositions which would ordinarily use butanoylcyclohexane derivatives defined according to the structure:

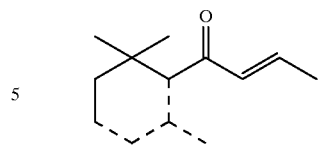

may now, instead, use for the most part or totally the trimethylcyclohexenylcyclopropyl ketones of our invention having the structure:

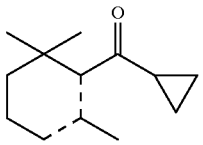

with the same organoleptic effects. Nevertheless, when such butanoylcyclohexane derivatives having the structure:

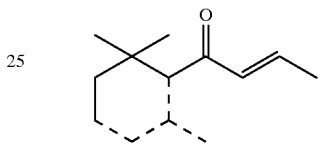

are used in conjunction with the trimethylcyclohexenylcyclopropyl ketones of our invention having the structure:

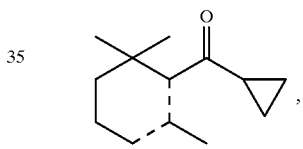

a synergistic effect takes place in formulating rose perfumes, wherein the perception of the rose aroma is increased more than the sum of the parts. Unfortunately, too high a use of butanoylcyclohexane derivatives having the structure:

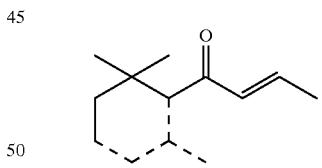

gives rise to a "sensitizing" effect, particularly when the wearer of the fragrance is exposed to sunlight. Accordingly, it is desirable to diminish the amount of butanoylcyclohexane derivatives having the structure:

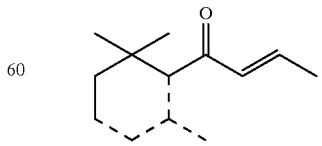

used while at the same time achieving an identical or even improved organoleptic (fragrance) effect. That improvement is effected by use of one or both of the trimethylcyclohexenylcyclopropyl ketones of our invention having the structure:

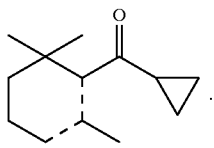

The compositions of matter of our invention produced according to the processes disclosed in the instant specification are capable of augmenting, enhancing or providing strong, non-sensitizing, persistent rose, sweet, woody, tobacco, dried fruit aromas with floral undertones to perfume compositions, colognes and perfumed articles (e.g., solid or liquid anionic, nonionic, cationic or zwitterionic detergents, fabric softener articles, dryer-added fabric softener articles, fabric softener compositions, cosmetic powders, hair preparations, perfumed polymers and the like).

The trimethylcyclohexenylcyclopropyl ketones of our invention may be prepared by means of a process of reacting a compound having the structure:

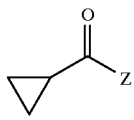

with 1,3,3-trimethylcyclohexene having the structure:

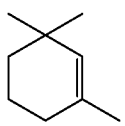

in accordance with the reaction:

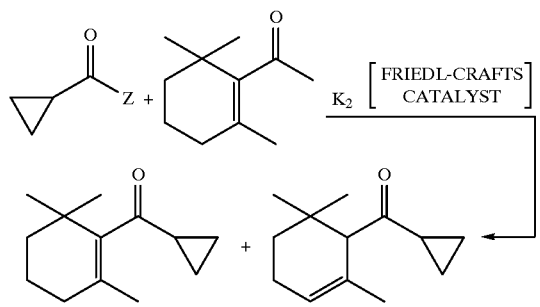

wherein Z represents chloro, bromo or the moiety:

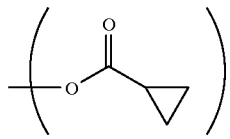

and wherein the Friedl-Crafts catalyst $K_2$ is one or a mixture of:

$ZnCl_2$;
$SnCl_4$;
$AlCl_3$;
$Al(C_2H_5)Cl_2$;
$TiCl_4$—$AlCl_3$;
$FeCl_3$;
$BF_3$; and
$BF_3(OC_2H_5)_2$.

Thus, the reactant having the structure:

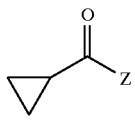

may be the compound having the structure:

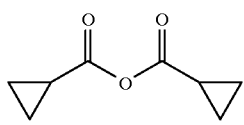

or the compound having the structure:

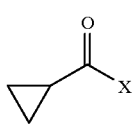

wherein X is cloro or bromo.

In the alternative, and more preferably, the compound having the structure:

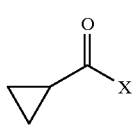

may be reacted with 1,3,3-trimethylcyclohexene having the structure:

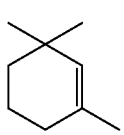

according to the reaction:

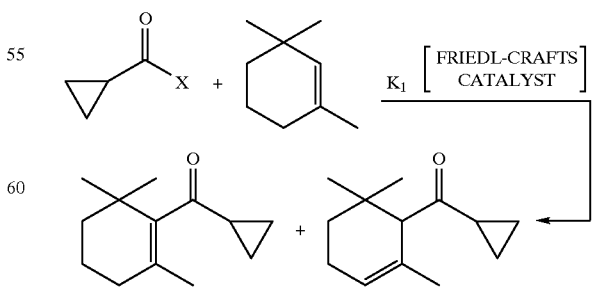

wherein X is chloro or bromo, and the catalyst $K_1$ is one or a mixture of:

ZnCl$_2$;
SnCl$_4$;
AlCl$_3$;
Al(C$_2$H$_5$)Cl$_2$;
TiCl$_4$—AlCl$_3$; and/or
FeCl$_3$.

Thus, only when using the reactant having the structure:

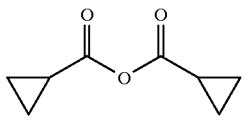

can the catalysts: BF$_3$ and BF$_3$(OC$_2$H$_5$)$_2$ be used for promoting the Friedl-Crafts reaction.

The most preferred reagents that the most preferred reactant is the compound having the structure:

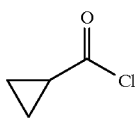

and the most preferred Friedl-Crafts catalyst is the catalyst, SnCl$_4$, and the most preferred reaction is:

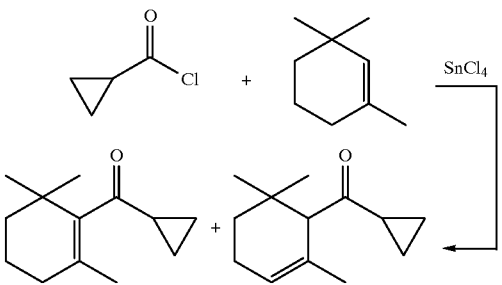

as shown in Example I, infra. In carrying out the reaction:

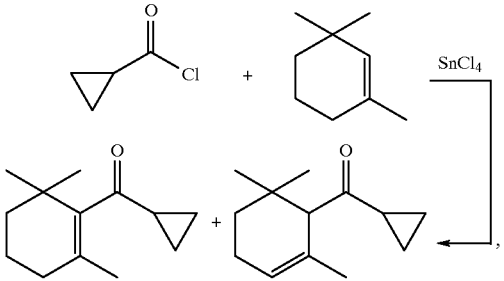

the percentage of compounds having the structure:

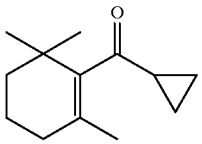

formed is from 15% up to 99%, and the percentage of compounds having the structure:

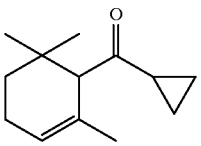

formed is from 85% down to about 15% by weight of the reaction mass.

The reaction is preferably carried out using equi-molar proportions of 1,3,3-trimethylcyclohexene having the structure:

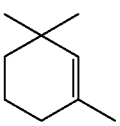

and the reagent having the structure:

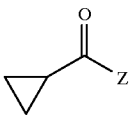

wherein Z is defined, supra; and a slight excess (approximately 10% by weight) of Friedl-Crafts catalyst such as stannic chloride.

The reaction is carried out in the presence of an inert solvent such as methylene dichloride where the compounds having the structure:

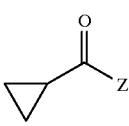

is first dissolved in the methylene dichloride and the resulting methylene dichloride solution is admixed with the 1,3,3-trimethylcyclohexene.

The reaction time varies between 2 and 5 hours, and the reaction temperature varies between 0° C. and 20° C.

At the end of the reaction, the reaction mass is neutralized with aqueous base such as a 10% sodium hydroxide solution. The organic phase is separated from the aqueous phase and the organic phase is stripped of solvent and then, preferably, fractionally distilled to yield the compounds having the structures:

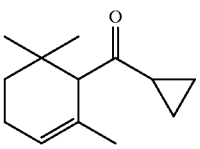 and 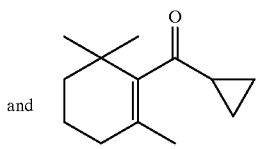

The mixture of compounds having the structures:

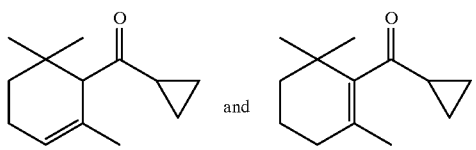

has a rose, sweet, woody, tobacco, dried fruit (fig-like; date-like) aroma with floral undertones.

One or more of the trimethylcyclohexenylcyclopropyl ketones of our invention prepared in accordance with the processes set forth, supra, and described in detail in Example I, infra, taken alone or in combination with one or more of the substances defined according to the structures:

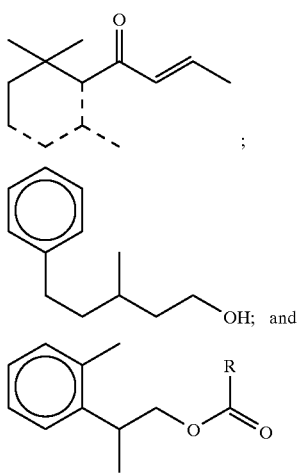

(wherein R and the dashed lines are defined, supra) and one or more auxiliary perfume ingredients including, for example, alcohols (other than the alcohol having the structure:

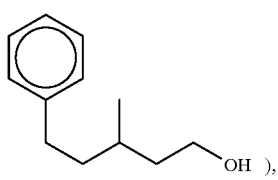

aldehydes, ketones (other than the trimethylcyclohexenyl-cyclopropyl ketones of our invention), terpenic hydrocarbons, nitrites, esters (other than the esters having the structure:

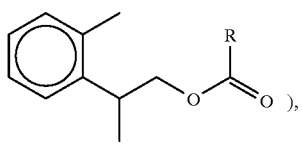

lactones, ethers, natural essential oils and synthetic essential oils may be admixed so that the combined odors of the individual components produce a pleasant and desired fragrance, particularly and preferably in the rose and woody cologne aroma field. Such compositions usually contain:

(a) the main note or the "bouquet" or foundation stone of the invention;
(b) modifiers which round off and accompany the main note;
(c) fixatives which include odorous substances which lend a particular note to the perfume throughout all stages of evaporation and substances which retard evaporation; and
(d) topnotes which are usually low boiling, fresh smelling materials.

In perfume compositions, it is the individual components which contribute their particular olfactory characteristics; however, the overall sensory effect of the perfume composition will be at least the sum total of the effects of each of the ingredients. Thus, the trimethylcyclohexenylcyclopropyl ketones of our invention, taken alone or in combination with the substances having the structures:

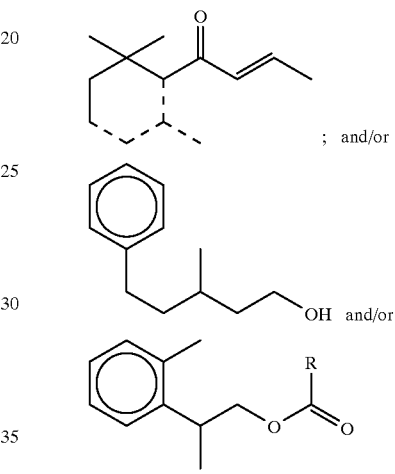

of our invention can be used to alter, modify or enhance the aroma characteristics of a perfume composition, for example, by utilizing or moderating the olfactory reaction contributed by another ingredient in the composition.

The amount of one or more of the trimethylcyclohexenyl-cyclopropyl ketones of our invention (taken in combination with the substances having the structures:

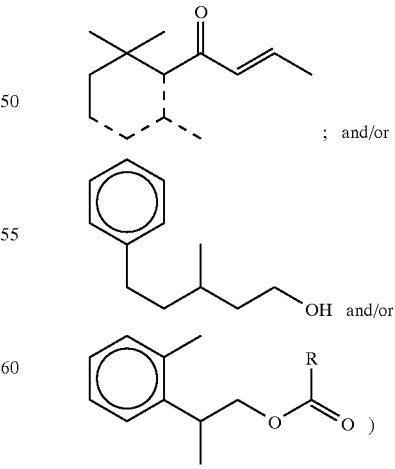

which will be effective in perfume compositions as well as in perfumed articles (e.g., anionic, nonionic, cationic or zwitterionic detergents, soaps, fabric softener compositions, fabric softener articles and perfumed polymers) and colognes depend upon many factors including the other ingredients, their amounts and the effects which are desired. It has been found that perfume compositions containing as little as 0.01% of one or both of the trimethylcyclohexenyl-cyclopropyl ketones of our invention or even less (e.g., 0.005%) can be used to impart, augment or enhance strong, nonsensitizing and persistent rose, sweet, woody, tobacco, dried fruit aromas with floral undertones to soaps, cosmetics, anionic, nonionic, cationic or zwitterionic detergents, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The trimethylcyclohexenylcyclopropyl ketones of our invention, prepared in accordance with the processes as set forth, supra (taken alone or taken together with other ingredients in perfume compositions), is (are) useful as (an) olfactory component(s) in detergents and soaps, space odorants and deodorants, perfumes, colognes, toilet waters, bath preparations such as creams, deodorants, hand lotions and sun screens; powders, such as talcs, dusting powders, face powders, microporous "perfumed" slow release polymers and the like.

When used as (an) olfactory component(s) in perfumed articles, as little as 0.005% of one or both of the trimethyl-cyclohexenylcyclopropyl ketones of our invention will suffice to impart, augment or enhance strong, nonsensitizing, persistent rose, sweet, woody, tobacco, dried fruit aromas with floral undertones. Generally, no more than 6% of one or both of the trimethylcyclohexenylcyclopropyl ketones of our invention based on the ultimate end product is required in the perfumed article. Generally, no more than 10% of the trimethylcyclohexenylcyclopropyl ketones of our invention, taken in combination with at least one of the substances defined according to the structures:

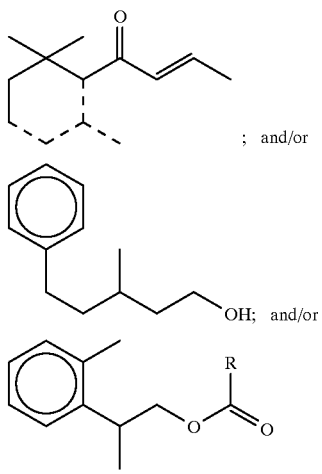

based on the ultimate end product is required in the perfumed article. Accordingly, the range of use of at least one of the trimethylcyclohexenylcyclopropyl ketones of our invention in perfumed articles, per se, is from about 0.005% up to about 6% by weight based on the perfumed article, and the range of use of at least one of the trimethylcyclohex-enylcyclopropyl ketones of our invention, taken in combination with at least one of the substances defined according to the structures:

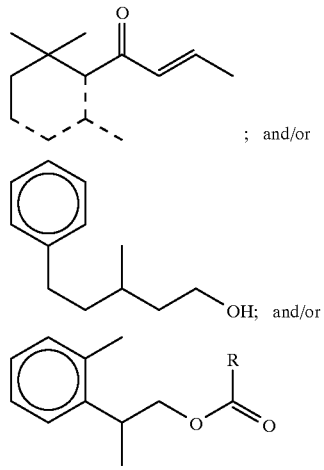

is from about 0.005% up to about 10% by weight based on a perfumed article.

In addition, the perfume composition or fragrance composition of our invention can contain a vehicle or carrier for one or both of the trimethylcyclohexenylcyclopropyl ketones of our invention. The vehicle can be a liquid such as a non-toxic alcohol, e.g., ethyl alcohol; a non-toxic glycol, e.g., propylene glycol or the like. The carrier can be an absorbent solid such as a gum (e.g., gum arabic, guar gum or xantham gum or combinations thereof) or components for encapsulating the composition (such as by coacervation) or using prepolymers such as urea-formaldehyde prepolymers which are able to form a urea-formaldehyde polymer capsule around a liquid perfume center.

It will thus be apparent that the trimethylcyclohexenyl-cyclopropyl ketones of our invention, taken alone or in combination with at least one of the substances defined according to the structures:

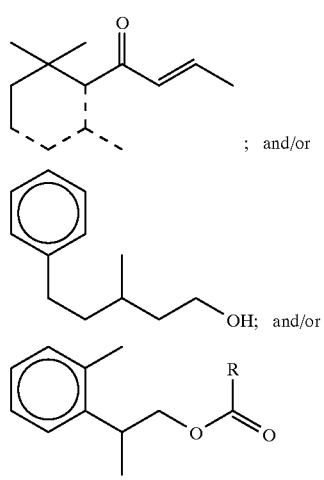

can be utilized to alter, modify or enhance sensory properties, particularly organoleptic properties such as fragrances of a wide variety of consumable materials.

The following Example I sets forth a means for preparing the trimethylcyclohexenylcyclopropyl ketones of our invention. The examples including and following Example I, infra, set forth illustrations of organoleptic utilities of the trimethylcyclohexenylcyclopropyl ketones of our invention, taken alone or in combination with at least one of the substances defined according to the structures:

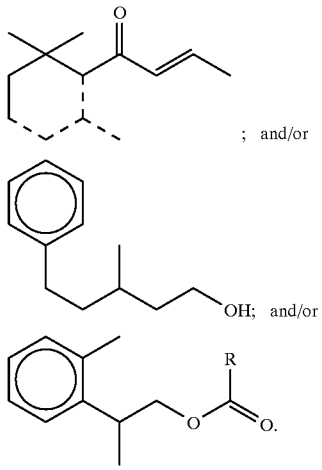

All parts and percentages given herein are by weight unless otherwise specified.

EXAMPLE I

PREPARATION OF A MIXTURE OF 2,6,6-TRIMETHYL-1-CYCLOHEXENE-1-YL KETONE AND 2,6,6-TRIMETHYL-1-CYCLOHEXENE-2-YL KETONE

Reaction:

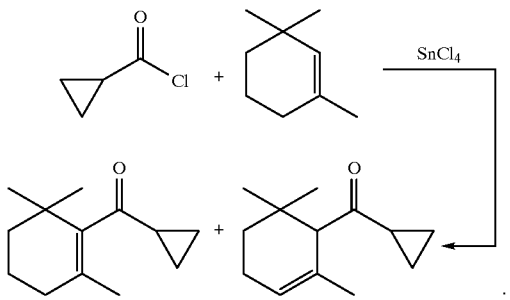

Into a 100 cc reaction flask equipped with stirrer, reflux condenser and thermometer is placed 10 grams (0.08 moles) of the compound having the structure:

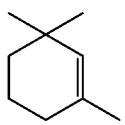

and 24 grams (0.09 moles) of stannic chloride dissolved in 90 ml of dichloromethane. The stannic chloride-dichloromethane-compound having the structure:

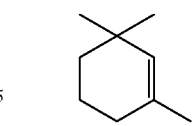

mixture is cooled to 0° C. Over a period of 1 hour while maintaining the reaction mass at a temperature of 0° C., the compound having the structure:

is added to the reaction mass with stirring. The reaction mass is then continued to be stirred at a temperature of between 0° C. and 10° C. for a period of 2 hours.

At the end of the 2 hour period, the pH of the reaction mass is 1.0. The reaction mass is neutralized with 20 ml of 10% sodium hydroxide solution. The reaction mass now exists in two phases, an organic phase and an aqueous phase.

The organic phase is washed with 170 cc portion of water. The methylene dichloride solvent is then stripped off and the reaction mass is distilled.

The GLC profile of the distillate (fractions 2–8) is set forth in FIG. 1, described in the DETAILED DESCRIPTION OF THE DRAWINGS, supra.

Bulked distillation fractions 2–5 have an excellent rose, sweet, woody, tobacco, dried fruit (fig-like; date-like) aroma with floral undertones.

EXAMPLE II

Rose Formulation

The following mixture is prepared:

| Ingredients | Parts by weight |
| --- | --- |
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| 1-Citronellal | 90.0 |
| Neryl acetate | 3.0 |
| Clove bud oil | 1.0 |
| Cadinene | 2.0 |
| Guaiene | 1.0 |
| Gum turpentine | 12.0 |
| α-Pinene | 1.0 |
| Myrcene | 5.0 |
| Limonene | 2.0 |
| p-Cymene | 1.0 |

To the foregoing mixture, 30 parts by weight of an 85:15 mixture of the compounds having the structures:

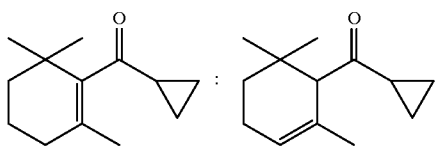

produced according to Example I, bulked distillation fractions 2–5 is added. The resulting mixture has an intense rose aroma with sweet, woody, tobacco, dried fruit and floral undertones.

EXAMPLE III

To the formulation of Example II, 30 parts by weight of the compound defined according to the structure:

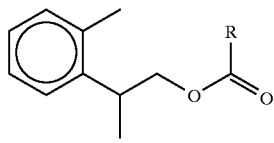

(wherein R is methyl) is added. The resulting mixture has an intense rose aroma with sweet, woody, tobacco, dried fruit undertones and a peony-like and lilac topnote.

EXAMPLE IV

To the formulation of Example II, 30 parts by weight of a 2% solution of 3-methyl-1-phenylpentanol-5 having the structure:

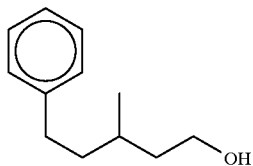

in diethylphthalate and 15 parts by weight of 0.01% solution of β-damascenone having the structure:

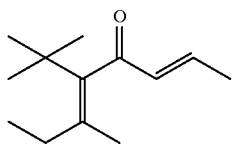

in diethylphthalate is added. The resultant mixture has a much brighter rose topnote and is fruitier and richer on dryout as compared with the same mixture without the composition of matter containing the 3-methyl-1-phenylpentanol-5 and the β-damascenone. Accordingly, the olfactory description of the formulation of this example can be described as follows:

a rich rose aroma with sweet, woody, tobacco, dried fruit and floral undertones and fruity and bright white rose topnotes.

EXAMPLE V

Preparation of Cosmetic Powder Composition

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
| --- | --- |
| The mixture of compounds defined according to the structures:<br><br>and<br> | An intense and substantive rose, sweet, woody, tobacco, dried fruit (fig-like; date-like) aroma with floral undertones. |
| prepared according to Example I. | |
| The perfume composition of Example II. | An intense rose aroma with sweet, woody, tobacco, dried fruit and floral undertones. |
| The perfume composition of Example III. | An intense rose aroma with sweet, woody, tobacco, dried fruit and a peony-like and lilac topnote. |
| The perfume composition of Example IV. | A rich rose aroma with sweet, woody, tobacco, dried fruit and floral undertones and bright white rose topnotes. |

EXAMPLE VI

Perfumed Liquid Detergents

Concentrated liquid detergents (Lysine salt of n-dodecybenzene sulfonic acid as more specifically described in U.S. Pat. No. 3,948,818 issued on Apr. 6, 1976 incorporated by reference herein) with aroma nuances as set forth in Table I of Example V are prepared containing 0.10%, 0.15%, 0.20%, 0.25%, 0.30% and 0.35% of the substance set forth in Table I of Example V. They are prepared by adding and homogeneously mixing the appropriate quantity of substance set forth in Table I of Example V in the liquid detergent. The detergents all possess excellent aromas as set forth in Table I of Example V, the intensity increasing with greater concentrations of substances as set forth in Table I of Example V.

EXAMPLE VII

Preparation of Cologne and Handkerchief Perfumes

Compositions as set forth in Table I of Example V are incorporated into colognes at concentrations of 2.0%, 2.5%, 3.0%, 3.5%, 4.0% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table I of Example V are imparted to the colognes and to the handkerchief perfumes at all levels indicated.

EXAMPLE VIII

PREPARATION OF SOAP COMPOSITION

100 Grams of soap chips [per sample] (IVORY® produced by the Procter & Gamble Company of Cincinnati, Ohio) are each mixed with 1 gram samples of substances as set forth in Table I of Example V until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table I of Example V.

EXAMPLE IX

Preparation of Solid Detergent Compositions

Detergents are prepared using the following ingredients according to Example I of Canadian Patent No. 1,007,948:

| Ingredients | Percent by Weight |
| --- | --- |
| NEODOL ® 45-14 (a $C_{12}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example V. Each of the detergent samples has an excellent aroma as indicated in Table I of Example V.

EXAMPLE X

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57% $C_{20-22}$ HAPS;
   22% isopropyl alcohol;
   20% antistatic agent; and
   1% of one of the substances as set forth in Table I of Example V, supra.

Fabric softening compositions prepared according to Example I at column 15 of U.S. Pat. No. 3,632,396 having the aroma characteristics as set forth in Table I of Example V, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example V is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added softener non-woven fabrics and these aroma characteristics are described in Table I of Example V, supra.

EXAMPLE XI

Hair Spray Formulations

The following hair spray formulation is prepared by first dissolving PVP/VA E-735 copolymer manufactured by the GAF Corporation of 140 West 51st Street, New York, N.Y. in 91.62 grams of 95% of food grade ethanol. 8.0 Grams of the polymer is dissolved in the alcohol. The following ingredients are added to the PVP/VA alcoholic solution:

| Ingredients | Percent by Weight |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table I of Example V, supra | 0.10 |

The perfuming substances as set forth in Table I of Example V add aroma characteristics as set forth in Table I of Example V which are rather intense and aesthetically pleasing to the users of the soft-feel, good-hold pump hair sprays.

EXAMPLE XII

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of the Union Carbide Corporation) (1.4 weight percent). The resulting melt is admixed with Stepanol WAT produced by the Stephan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table I of Example V is added to the mixture. The resulting mixture is cooled to 40° C. and blending is carried out for an additional one hour in each case. At the end of this blending period, the resulting material has a pleasant fragrance as indicated in Table I of Example V.

What is claimed is:

1. A mixture of a trimethylcyclohexenylcyclopropyl ketone according to the following structure:

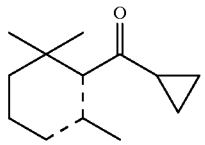

wherein one of the dashed lines is a carbon—carbon double bond and the other of the dashed lines is a carbon—carbon single bond and an adjuvant therefor which is selected from the group consisting of substances defined according to the structures:

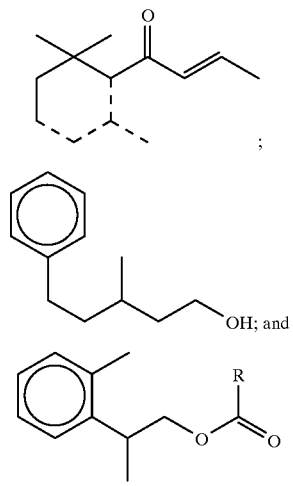

wherein R is methyl or ethyl and in the structure:

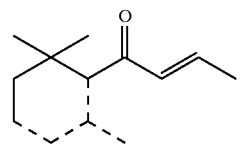

one or two of the dashed lines represent carbon—carbon double bonds and the other of the dashed lines represent carbon—carbon single bonds with the proviso that when the dashed lines represent two carbon—carbon double bonds, said carbon—carbon double bonds are conjugated.

2. A process for augmenting, enhancing or imparting an aroma in or to a consumable material selected from the group consisting of perfume compositions, perfumed articles and colognes comprising the step of admixing with said consumable material an aroma augmenting, enhancing or imparting quantity of at least one trimethylcyclohexenyl-cyclopropyl ketone.

3. A process for augmenting, enhancing or imparting aroma in or to a consumable material selected from the group consisting of perfume compositions, perfumed articles and colognes comprising the step of admixing with said consumable material an aroma augmenting, enhancing or imparting quantity of the mixture according to claim 1.

4. A consumable material selected from the group consisting of perfume compositions, perfumed articles and colognes comprising a consumable material base and admixed therewith an aroma augmenting, enhancing or imparting quantity of at least one trimethylcyclohexenylcy-clopropyl ketone defined in claim 1.

5. A consumable material selected from the group consisting of perfume compositions, perfumed articles and colognes comprising a consumable material base and admixed therewith an aroma augmenting, enhancing or imparting quantity of the mixture according to claim 1.

* * * * *